United States Patent [19]
Graham et al.

[11] Patent Number: 5,632,773
[45] Date of Patent: May 27, 1997

[54] BIOSTABLE CORNEAL IMPLANTS

[75] Inventors: Richard S. Graham, Irvine; Crystal M. Cunanan, Mission Viejo, both of Calif.

[73] Assignee: Allergan, Inc., Irvine, Calif.

[21] Appl. No.: 616,786

[22] Filed: Mar. 15, 1996

Related U.S. Application Data

[63] Continuation of Ser. No. 237,088, May 3, 1994, abandoned.

[51] Int. Cl.$^6$ ..................................................... A61F 2/14
[52] U.S. Cl. ............................. 623/5; 623/6; 523/105; 523/108
[58] Field of Search ..................... 623/5, 6; 523/105, 523/108; 427/2.1, 2.24

[56] References Cited

U.S. PATENT DOCUMENTS

| | | |
|---|---|---|
| 4,388,428 | 6/1983 | Kuzma et al. |
| 4,589,964 | 5/1986 | Mayhan et al. |
| 4,806,382 | 2/1989 | Goldberg et al. |
| 4,845,132 | 7/1989 | Masuoka et al. |
| 4,919,659 | 4/1990 | Horbett et al. |
| 4,961,954 | 10/1990 | Goldberg et al. |
| 4,983,181 | 1/1991 | Civerchia . |
| 5,002,582 | 3/1991 | Guire et al. ............................. 623/901 |
| 5,112,350 | 5/1992 | Civerchia et al. ........................ 623/5 |
| 5,192,316 | 3/1993 | Ting . |
| 5,201,764 | 4/1993 | Kelman et al. ........................... 623/6 |
| 5,433,745 | 7/1995 | Graham et al. ........................... 623/5 |

OTHER PUBLICATIONS

Hino et al, A Study on Collagen–Plastic Composites as Biomaterials, "Biocompatability of Tissue Analogs", vol. II, pp. 71–87.

Suzuki et al, Graft Copolymerization of Acrylamide onto a Polyethylene Surface Pretreated with a Glow Discharge, Macromolecules 1986, 1804–1808.

Yeh et al, Blood compatibility of surface modified by plasma polymerization, Journal of Biomedical Materials Research, vol. 22, 795–818 (1988).

Petit et al, Quanitation of Rabbit Corneal Epithelial Cell Outgrowth on Polymeric Substrates in Vitro, "Investigative Opthalmology & Visual Science,"vol. 31, No. 11, Nov. 1990.

Horbett et al, Hydrophilic–Hydrophobic Copolymers as Cell Substrates: Effect on 3T3 Cell Growth Rates, Journal of Colloid and Interface Science, vol. 104, No. 1, Mar. 1985.

Dreyfuss et al, Graft Polymers, vol. 7, pp. 551–579 Encyclopedia of Polymer Science and Engineering.

Gombotz et al, Gas–Discharge Techniques for Biomaterial Modification, vol. 4, Issue 1 (1987) pp. 1–42, "Critical Reviews in Biocompatibility".

Lydon et al, Cellular interactions with synthetic polymer surfaces in culture, Biomaterials 1985, vol. 6 Nov., pp. 396–402.

Kaplan et al, Medical Polymers and Plasma Technology, Technical Notes, Plasma Science, Foster City, California pp. 1–5.

On The Surface, vol. II, No. I, Improved Biocompatibility by Surface Modification, Metro–Line Industries, Inc. Corona, California.

Special Report, Using Gas Plasma to Reengineer Surfaces, Nancy B. Mateo, Reprinted from Medical Product Manufacturing News, Sep./Oct. 1990 pp. 1–2.

(List continued on next page.)

*Primary Examiner*—Paul B. Prebilic
*Attorney, Agent, or Firm*—Frank J. Uxa

[57] ABSTRACT

Corneal implants and methods for producing such implants are disclosed. The present corneal implants comprise a lens body which is optically clear and is structured to be surgically attached in or on the cornea of a mammalian eye, the lens body including a hydrogel composition containing water, a collagen component and a polymeric material covalently bonded to the collagen component. The hydrogel composition has enhanced biostability relative to an identical hydrogel composition without the polymeric material.

13 Claims, 1 Drawing Sheet

OTHER PUBLICATIONS

Dekker et al, Adhesion of endothelial cells and adsorption of serum proteins of gas plasma–treated polytetrafluoro–ethylene, Biomaterials 1991, vol. 12 Mar., pp. 130–138.

H. Boenig, Plasma Polymerization, vol. 11, pp. 249–261, Academic Press, Inc., Orlando, Fla, 1986 Encyclopedia of Polymer Science and Engineering.

Ratner et al, Plasma Deposition and Treated for Biomaterial Applications "Plasma Deposition of Polymer Films", Academic Press, Boston, 1989.

BIOSTABLE CORNEAL IMPLANTS

This application is a continuation of U.S. patent application Ser. No. 08/237,088, filed May 3, 1994 now abandoned.

BACKGROUND OF THE INVENTION

The present invention relates to corneal implants and methods for producing such implants. In particular, the invention relates to corneal implants structured to be surgically attached in or on the cornea of a mammalian eye which include a hydrogel composition and which have enhanced biostability.

The cornea comprises five layers, including an outer layer of epithelial cells, Bowman's membrane immediately posterior of the cells, the stroma immediately posterior of Bowman's membrane, Descemet's membrane immediately posterior of the stroma and the endothelium immediately posterior of Descemet's membrane. A number of surgical operations involve implanting a corrective lens structure into or onto one or more of these corneal components. For example, in one form of eye surgery, the layer of epithelial cells is removed and a corrective lens structure is placed and secured at the location where the cells were removed. In another form of eye surgery, the layer of epithelial cells is removed and then a wedge-shaped annulus from Bowman's membrane and the underlying stroma is removed. An incision is then made from the posterior end of the resulting groove radially outwardly in an annual zone to define a flap. A corrective lens structure is attached by inserting the wing of the lens structure beneath the corneal flap and fixing, e.g., suturing, it in place. In addition, a corrective lens structure can be placed entirely within the stroma. This surgical procedure involves making an incision in the cornea to gain access to the stroma and also involves disrupting the stroma by placing a lens structure therein.

In each of these surgical procedures, it is highly desirable, even necessary, for the long term viability of such lens onlays or implants that the cornea, e.g., the epithelial cells and/or stromal keratocytes, grow onto the lens structure and/or adhere to the lens structure. Achieving such growth and adhesion has been one substantial problem inhibiting the use of such corneal onlay and implant procedures.

Hydrogel compositions have been suggested for use as materials of construction for corneal implants. As used herein, the term "hydrogel composition" refers to a composition including a material, for example, a polymeric material, and sufficient amount of water to cause the composition to swell relative to the anhydrous material. Such hydrogel compositions often include at least about 38% by weight of water, and may include as much as about 60% or about 80% or about 90% or more by weight of water. One concern of using hydrogel compositions as corneal implants is the relative inability of such compositions to support the growth and/or adhesion of epithelial cells on and/or to the implants.

One hydrogel composition that has been suggested for use in corneal implants is a hydrogel of water and collagen. Such a hydrogel composition has a sufficient nutrient, for example, glucose, diffusivity, and cytophilicity, that is the ability to support at least one of epithelial cell growth and epithelial cell adhesion, to be useful in corneal implants. One problem which has become apparent with such collagen hydrogels is a substantial susceptibility to being degraded by enzymes present in the eye. This is a significant concern since the corneal implant is surgically attached to the eye and is intended for long term, even permanent, placement in the eye.

Therefore, it would be advantageous to provide hydrogel compositions for use in corneal implants which have many, if not all, of the beneficial properties of hydrogels of collagen and water and, in addition, have enhanced biostability relative to such collagen/water hydrogels.

SUMMARY OF THE INVENTION

New corneal implants and methods for producing such implants have been discovered. The present invention takes advantage of the attractive properties of collagen/water hydrogel compositions as corneal implant materials of construction while, at the same time, providing corneal implants which have enhanced biostability relative to such collagen/water hydrogel compositions. The present modifications, as described hereinafter, render lens structures which comprise hydrogel compositions with such enhanced biostability and sufficient ability to support the growth of corneal epithelial cells, thus making such lens structures useful as synthetic epikeratophakia lenses. The present methods are straightforward and easy to practice. Further, these methods are very flexible in that one or more steps can be modified to predictably alter the properties of the resulting hydrogel composition and corneal implant to meet the requirements of the specific application at hand.

In one broad aspect of the present invention, corneal implants are provided comprising a lens body which is optically clear and is structured to be surgically attached in or on the cornea of a mammalian eye. This lens body includes a hydrogel composition comprising water, a collagen component and a polymeric material, which includes one polymer or more than one polymer, having increased hydrophobicity relative to the collagen component covalently bonded to, preferably grafted onto, the collagen component. This hydrogel composition has enhanced biostability relative to an identical hydrogel composition without the polymeric material. It has surprisingly been found that the present hydrogel compositions have such enhanced biostability while also having acceptable and sufficient properties, such as optical clarity, high water content, nutrient (glucose) diffusivity, mechanical strength, cytophilicity and the like, so as to be useful in corneal implants.

As used herein, the term "biostability" refers to the ability of a material, such as a hydrogel composition making up a corneal implant, to resist the action of proteolytic enzymes present in a mammalian, for example, human, eye. Such proteolytic enzymes tend to degrade or otherwise cause the deterioration of collagen-containing corneal implants in the eye.

In one particularly useful embodiment, the present corneal implants include lens bodies including hydrogel compositions which further comprise an amount, preferably a minor amount, of a linked component covalently bonded to both of the collagen component and the polymeric material. This linked component, which is derived from a bifunctional monomeric component, is effective to further enhance the biostability of the hydrogel composition relative to an identical hydrogel composition without the linked component.

In another broad aspect of the present invention, methods for producing corneal implants in the form of lens bodies which are optically clear and are structured to be surgically implanted in or on the cornea of a mammalian eye are provided. Such methods comprise forming a mixture comprising collagen and a monomeric component. This mixture is subjected to conditions effective to polymerize the monomeric component and to covalently bond, preferably graft, a polymeric material, which includes one polymer or more than one polymer, derived from the monomeric component to a collagen component derived from the collagen in the mixture and form a composite. The polymeric material derived from this monomeric component has increased hydrophobicity relative to the collagen component. A hydrogel composition is formed which comprises water and the composite. This hydrogel composition has enhanced biostability relative to an identical hydrogel composition without the polymeric material.

These and other aspects and advantages of the present invention are set forth in the following detailed description and claims, particularly when considered in conjunction with the accompanying drawings in which like parts bear like deference numerals.

DETAILED DESCRIPTION OF THE INVENTION

Figure 1:
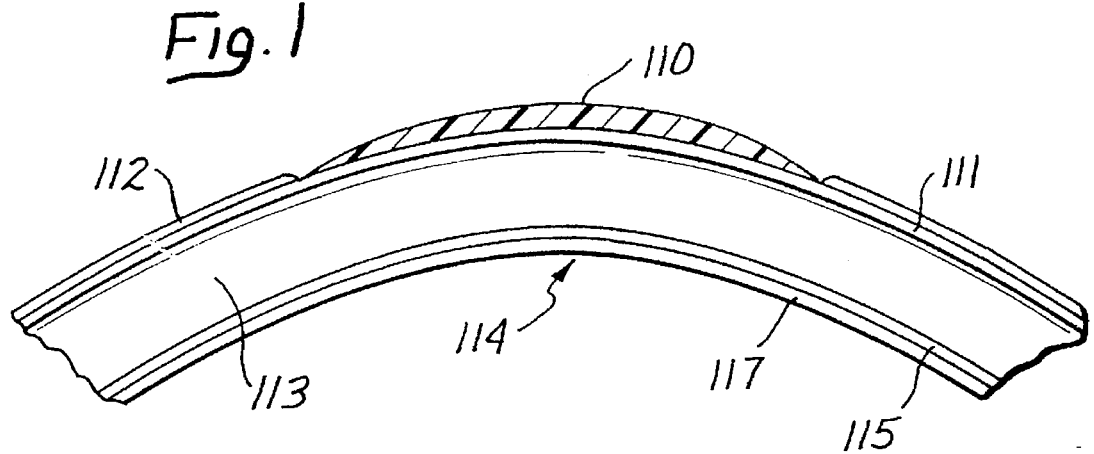
FIG. 1 is an enlarged axial, cross-sectional view showing an ocular device according to the present invention attached to a cornea.

The present invention relates to corneal implants which comprise a lens body that is optically clear and is structured to be surgically attached in or on the cornea of a mammalian eye. Such lens bodies include a hydrogel composition comprising water, a collagen component and a polymeric material, preferably a cross-linked polymeric material, covalently bonded, preferably grafted, to the collagen component. This polymeric material is selected to have increased hydrophobicity relative to the collagen component. That is, the polymeric material is more hydrophobic (or less hydrophilic) than is the collagen component. In other words, the polymeric material has a reduced ability, relative to the collagen component, to combine with or otherwise associate with water. Preferably, the hydrophobic polymeric material is such as to be non-hydrogel forming, that is the polymeric material by itself preferably does not form a hydrogel with water. The resulting hydrogel has enhanced biostability relative to an identical hydrogel composition without the polymeric material.

The hydrophobic polymeric material is derived from a monomeric component. In one embodiment, the monomeric component has the same degree of polarity or less polarity relative to the polarity exhibited by methyl methacrylate. For example, such "non-polar" monomeric components have a fractional polarity (as defined by Lydon et al, Biomaterials, 6:396, 1985) equal to or less than the fractional polarity of methyl methacrylate. The monomeric component preferably is selected from compounds having functional carbon-carbon unsaturation, for example, a polymerizable carbon—carbon double bond, i.e., >C=C<. The polymers formed by the polymerization of such monomeric components have increased hydrophobicity relative to the collagen components of the present compositions. Particularly useful monomeric components include olefins, acrylates, methacrylates, substituted counterparts thereof and mixtures thereof. As used herein, the term "substituted counterpart thereof" refers to a similar compound or derivative thereof which includes one or more substituents in which one or more hydrogen atoms are replaced by one or more other species including, but not limited to, monovalent hydrocarbon groups, such as alkyl, alkenyl and alkynyl (such as ethenyl, propenyl, butenyl, ethynyl and the like unsaturated hydrocarbon groups having 2 to about 6 or more carbon atoms) and aryl heterocyclic groups; halo such as F, Cl, Br and I; $NH_2$; $NO_2$; alkoxy; alkylthio; aryloxy; arylthio; alkanoyl alkanoyloxy; aroyl; aroyloxy; acetyl; carbamoyl alkylamino; dialkylamino; arylamino; aklylarylamino diarylamino; alkanoylamino; alkylsulfinyl; alkylsulfenyl alkylsufonyl; alkylsulfonylamido; azo; benzyl; carboxy; cyano; guanyl; guanidino; imino; phosphinyl; silyl; thioxo; ureido or vinylidene or where one or more carbon atoms are replaced by one or more other species including, but not limited to, species containing N, P, O or S.

In one embodiment, the substituents included in the monomeric components are preferably made up of carbon and hydrogen atoms. In addition, the ester groups of the acrylates and methacrylates are preferably made up of carbon and hydrogen atoms. Further, if a hetero atom, such as N, P, O and S, is included, the polarity resulting from such hetero atom is preferably reduced (or covered) by the presence of a relatively bulky hydrocarbyl group, such as an aryl-containing group.

Specific examples of monomeric components include ethylene, propylene, butylene, styrene and the like olefins; acrylic acid; methyl acrylate, ethyl acrylate, trifluouro ethyl acrylate, butyl acrylate, and the like alkyl acrylates and substituted alkyl acrylates; methacrylic acid; methyl methacrylate, dimethyl methacrylate, ethyl methacrylate, (2-(dimethylaminoethyl) ethyl methacrylate), (3-sulfopropyl methacrylate, potassium salt), (2,2,2-trifluoroethyl methacrylate), 3-methacryl-oxypropyl-tris (trimethoxysiloxy) silane, and the like alkyl methacrylates and substituted alkyl methacrylates and mixtures thereof.

The monomeric component is present in an amount effective to produce a polymeric material covalently bonded to the collagen component. The amount of the polymeric material is effective to enhance the biostability of a hydrogel composition including such polymeric material/collagen component composite relative to an identical hydrogel composition without the polymeric material. The amount of monomeric component (and polymeric material) used varies depending on a number of factors, for example, the specific monomeric component being employed, the specific degree of biostability desired, the reaction conditions and processing employed and the like. The amount of monomeric component (and polymeric material) used should be such as to have no substantial or undue detrimental effect on the usefulness of the final hydrogel composition as a corneal implant material of construction. Preferably, the monomeric component (or polymeric material) is present in an amount in the range of about 20% to about 300% by weight of the amount of collagen (or collagen component) present. Particularly useful results are obtained if the amount (by weight) of the monomeric component (or polymeric material) employed is at least equal to the collagen (or collagen component) used.

Collagen is a major protein of connective tissue such as skin, cornea, etc. Preferably, the collagen employed to produce the present composites is at least partially, more preferably substantially completely, soluble in the precursor mixture. Collagen can be solubilized, separated and purified by the treatment with proteolytic enzymes (other than collagenase).

Solubilized collagen may be defatted to the extent necessary to obtain an optically clear material. Solubilized collagen contains many $NH_2$ and $COOH$ groups in its structure, and chemical modifications of the molecule can be readily made. For example, all or some of the amino groups may be acrylated by reaction with a mixture of acetic anhydride and acetic acid, or other anhydride such as succinic anhydride. All or some of the carboxyl groups contained in the molecule may be esterified by the standard reaction with acidified alcohol, preferably a water soluble aliphatic alcohol, such as methanol, ethanol, etc.

The polymeric material is preferably cross-linked. To obtain this cross-linking, the mixture preferably includes a cross-linker component, many of which are conventional and well known in the art. The cross-linker component is present in an amount effective to react with the polymeric material and/or monomeric component and to form covalently bonded cross-links in the polymeric material, thereby cross-linking the polymeric material.

Examples of useful cross-linker components include, for instance, ethylene glycol diacrylate, ethylene glycol dimethacrylate, 1,4-butylene dimethacrylate, 1,3-butylene dimethacrylate, 1,4-butylene dimethacrylate, propylene glycol diacrylate, propylene glycol dimethacrylate, diethylene glycol dimethacrylate, dipropylene glycol dimethacrylate, diethylene glycol diacrylate, diethylene glycol crotonate, allyl maleate, triallyl melamine, N,N'-methylenebisacylamide, glycerine trimethacrylate, divinyl ether, diallyl itaconate, ethylene glycol diester of itaconic acid, polyallyl glucose, for example, triallyl glucose, polyallyl sucrose, for example, pentsallyl sucrose, sucrose diacrylate, glucose dimethacrylate, pentaerythritol tetraacylate, sorbitol dimethacrylate diallyl aconitase, divinyl citraconate, diallyl fumarate, reactive monomers, allyl methacrylate, allyl acrylate, vinyl methacrylate and the like. Preferably, the cross-linker component is selected so as to be substantially non-reactive with the collagen and collagen component.

The amount of cross-linker component used varies depending upon a number of factors, for example, the specific cross-linker component being employed, the specific degree of biostability desired, the reaction conditions and processing employed, and the like. The amount of cross-linker component used should be such as to have no substantial or undue detriment effect on the usefulness of the final hydrogel composition as a corneal implant material of construction. Preferably, the cross-linker component is present in an amount in the range of about 0.1% to about 5% by weight of the amount of the monomeric component (or polymeric material) present.

The combination of collagen and the polymeric material provide a hydrogel composition which has enhanced biostability relative to an identical hydrogel composition without the polymeric material. Such enhanced biostability is obtained without substantially detrimentally affecting the other properties of a collagen hydrogel which make such material effective as a corneal implant material of construction. In other words, the present hydrogel compositions have enhanced biostability and, in addition, other properties so that such hydrogel compositions are useful in corneal implants. Such other properties include, for example, optical clarity, cytophilicity, nutrient, e.g., glucose, diffusivity and good mechanical properties.

In a particularly useful embodiment, the mixtures used to produce the present composites further include an amount of a bifunctional monomer component which is present in an amount effective to produce a linked component in the present composites effective to further enhance the biostability of the hydrogel compositions comprising water and the composites. The linked component is covalently bonded to both the collegan component and the polymeric material. Thus, the bifunctional monomeric component is sufficiently reactive to react with both the collagen component and the polymeric material. Such bifunctional monomeric components have two reactable groups per molecule, with one reactable group being effective to react and covalently bond to the collagen component and the other reactable group being effective to react and covalently bond to the polymeric material. Without wishing to limit the invention to any particular theory of operation, it is believed that the linked component derived from the bifunctional monomeric component facilitates the formation of a structure which further protects the collagen component from enzyme attack.

Any suitable bifunctional monomeric component may be employed, provided that it functions as described herein and has no substantial detrimental effect on the composite, the hydrogel composition and the corneal implant in which the resulting linked component is included. Examples of useful bifunctional monomeric components include glycidyl acrylate, glycidyl methacrylate, acrolein, aldehydes—such as crotonaldehyde, cinnamaldehyde and the like, diacetone acrylamide, vinyl benzyl chloride, methacrylic anhydride, acrylic anhydride, maleic anhydride, acrylated glycidyl ether, 1,4-butanediol diglycidyl ether, phenyl glycidyl ether, butyl glycidyl ether, bis phenol-A diglycidyl ether, epoxidized linseed oil, other epoxidized oils and the like.

The amount of bifunctional monomeric component used varies depending on a number of factors, for example, the specific bifunctional monomeric component being employed, the specific degree of biostability desired, the reaction conditions and processing employed and the like. The amount of bifunctional monomeric component used should be such as to have no substantial or undue detrimental effect on the usefulness of the final hydrogel composition as a corneal implant material of construction. Preferably, the bifunctional monomeric component is present in an amount in the range of about 0.1% to about 20%, more preferably about 2% to about 15%, by weight of the amount of the monomeric component present.

The preparation of the present hydrogel compositions is preferably effected in an aqueous medium or in a medium comprising water and alcohol which is miscible and compatible with water, such as methanol, ethanol, isopropanol and the like, and in which the other components form a clear solution or gel, desirably under an inert gas such as nitrogen and the like. In the practice of the process invention, it is desirable to form an aqueous solution or gel of the collagen. Such solutions or gels will generally contain less than about 30% by weight collagen because of the highly viscous nature of the mixture. Thus, an aqueous solution comprising up to about 15 weight percent collagen is suitable. A solution or dispersion or gel which contains about 0.5% to about 15%, preferably about 1% to about 13.5% by weight of collagen based on the total weight of the mixture is particularly useful.

The reaction conditions can vary depending, to a significant degree, on the reactants, catalyst, liquid medium and the like employed. In general, conventional types of polymerization known in the art can be employed, such as polymerization by high energy radiation, for example, gamma or ultraviolet radiation; solution polymerization in which the mixture comprises collagen, monomeric component, cross-linker component, bifunctional monomeric component and gamma or ultraviolet radiation; and the like polymerization techniques. Each specific type of polymerization generally requires a specific set of conditions. For example, when gamma radiation is used, the polymerization desirably is carried out at low temperature (under 30° C. and preferably below about 15° C.) and under an inert atmosphere in order to minimize degradation of the collagen due to high energy radiation. The resulting product is usually leached and equilibrated in an aqueous medium to remove traces of unreacted and/or catalytic residues, etc.

The reaction contacting, that is the polymerization of the monomeric component and polymeric material/collagen component covalent bonding, is preferably effected using a mixture containing about 50% to about 70% more preferably about 50% to about 60% by weight of solubilized collagen, about 50% to about 30% preferably about 50% to about 40% by weight of the monomeric component, based on the total charge of reactants, that is the collagen, monomeric component, cross-linker component and bifunctional monomeric component, if present.

The reactants, i.e., collagen, monomeric component, cross-linker component, and bifunctional monomeric component, if employed, are preferably miscible or soluble or partially soluble in water or soluble in a compatible water-organic liquid medium such as water-lower alkanol mixture. In a useful embodiment, the mixture further comprises a minor amount of an additional component effective to increase the solubility of the monomeric component in the mixture. Examples of such additional components include oxygen-containing materials, such as sugars, starches, ketones and the like. Specific examples include sucrose, dextran and methyl vinyl ketone and the like.

The amount of additional component used varies depending on a number of factors, for example, the specific monomeric component being employed, the specific degree of biostability desired, the reaction conditions and processing employed and the like. The amount of additional component used should be such as to have no substantial or undue detrimental effect of the usefulness of the final hydrogel composition as a corneal implant material of construction. Preferably, the additional component, if any, is present in an amount in the range of about 5% to about 100%, more preferably about 10% to about 75%, by weight of the monomeric component employed.

After the composite has been formed, the collagen component may be cross-linked to provide even further biostability. One drawback to such cross-linking after composite formation is that the resulting cross-linked collagen-containing composite has reduced cytophilicity and nutrient diffusivity, making such composite less effective as a corneal implant material of construction. However, a limited degree of such collagen component cross-linking may be useful in applications where biostability is of paramount importance and/or where nutrient diffusivity and/or cytophilicity may be sacrificed to a limited extent to achieve enhanced biostability.

In the event that the collagen component in the formed composite is to be cross-linked, conventional protein cross-linkers, such as those conventionally used to cross-link collagen may be employed. Examples include aldehydes, for example, formaldehyde, glutaraldehyde, glyoxal and the like; polyglycidyl ethers, such as poly glycerol poly glycidyl ethers and the like; dimethyl pimelimidate, and the like.

The amount of protein cross-linker component used varies depending on a number of factors, for example, the specific protein cross-linker component being employed, a specific degree of biostability desired and the like. The amount of protein cross-linker component used should be such as to have no substantial or undue detrimental effect on the usefulness of the final hydrogel composition as a corneal implant material of construction. Preferably, the protein cross-linker component is present in an amount in the range of about 0.01% to about 5% by weight of the collagen component present.

The collagen component in the composite may be cross-linked with the protein cross-linker component in any suitable manner, for example, contacting the collagen component-containing composite and the protein cross-linker component in a manner and at effective conditions which are conventionally employed to cross-link collagen, to provide the desired degree to collagen component cross-linking.

The presently useful hydrogel compositions can possess a water content as high as about 95%, based on the total weight of the hydrogel composition. In general, the present hydrogel compositions are characterized by optical clarity, high biocompatibility with living, in particular corneal, tissue, high biostability, high nutrient diffusivity and good mechanical properties.

The use of gamma radiation to effect the polymerization of the monomeric component and the covalent bonding of the polymeric material to the collagen component can be accomplished by conducting the subjecting step in the presence of gamma radiation at conditions effective for such proposes.

Chemical methods can be employed and may involve functionalizing, if necessary, the monomeric component or components from which the polymeric material is derived. Such functionalizing is effective so that a chemical reaction can take place between the collagen and the monomeric component or components from which the polymeric material is to be derived.

Referring now to FIG. 1, an ocular device in the form of a corneal onlay, shown generally at 110, is situated on and attached (sutured) to the Bowman's membrane 111 of a living cornea 114. Corneal onlay 110 is made in a mold in accordance with Example 1 and has the chemical make-up and properties of a hydrogel composition produced from the composition of Example 1. Also included in cornea 114 is epithelial cell layer 112, stroma 113, Descemet's membrane 115 and the endothelium 117. Corneal onlay 110, which is structured to correct one or more vision problems caused by defects in cornea 114 or in one or more other components of the eye, is set in place by surgically stripping or abrading away a desired area of the epithelial cell layer 112, placing corneal onlay 110 on this stripped area and securing corneal onlay 110 in place by suturing it to Bowman's membrane 111. The onlay 110 is placed with respect to the cornea 114 as shown in FIG. 1, so that the corneal onlay 110 is coaxial with the optical axis of the eye.

Once this surgical procedure is accomplished, epithelial cell layer 112 grows onto and attaches or adheres to corneal onlay 110.

Figure 2:
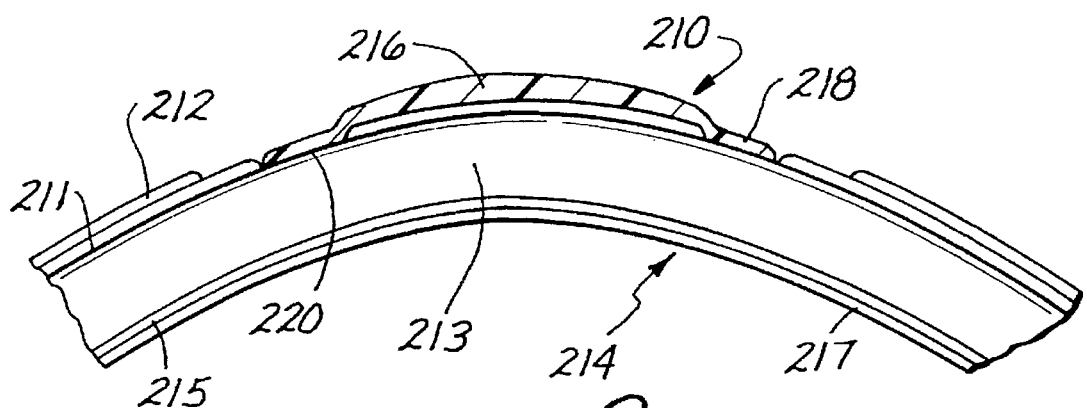
FIG. 2 is an enlarged axial, cross-sectional view showing another ocular device according to the present invention attached to a cornea.

Referring now to FIG. 2, an ocular device in the form of an alternate corneal onlay or epikeratophakia lenticula, shown generally at 210, is situated on and attached (sutured) to the Bowman's membrane 211 of a living cornea 214. Each element of cornea 214 in FIG. 2 which is also shown as an element of cornea 114 in FIG. 1 has a reference numeral increased by 100 relative to the same element shown in FIG. 1.

Corneal onlay 210 is made of substantially the same material as is corneal onlay 110. Corneal onlay 210 comprises a circular optic 216 and an annular wing 218 surrounding the optic. The onlay 210 is placed with respect to the cornea 214 as shown in FIG. 2, with the optic 216 being coaxial with the optical axis of the eye and with the annular wing 218 being received in an annular abraded zone 220. This zone 220 is obtained by stripping and/or abrading a portion of the epithelial cell layer 212 and the Bowman's membrane 211. A useful apparatus and procedure for performing this stripping/abrading are described in commonly assigned U.S. patent application Ser. No. 102,344, filed Sep. 29, 1987, which is incorporated in its entirety herein by reference.

Corneal onlay 210, and in particular optic 216, is structured to correct one or more problems caused by defects in cornea 214 or in one or more other components of the eye.

Once the surgical procedure of securing corneal onlay 210 in place as shown in FIG. 2 is accomplished, epithelial cell layer 212 grows onto corneal onlay 210 and attaches or adheres to corneal onlay 210.

Corneal onlay 210 is made of substantially the same material as is corneal onlay 110.

Figure 3:
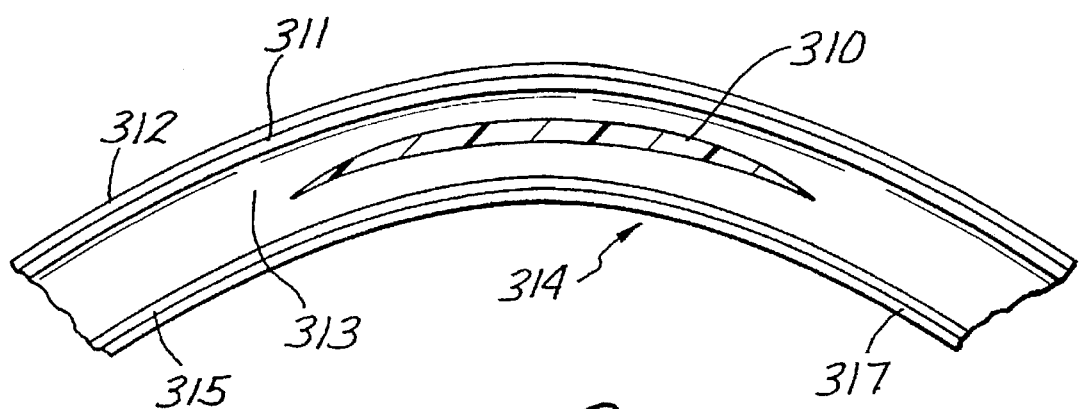
FIG. 3 is an enlarged axial, cross-sectional view showing an ocular device according to the present invention inserted in the stroma of a cornea.

Referring now to FIG. 3, an ocular device in the form of an intrastromal lens, shown generally at 310, is situated in the stroma 313 of living cornea 314. Each element of cornea 314 in FIG. 3 which is also shown as an element of corneal 114 in FIG. 1 has a reference numeral increased by 200 relative to the same element shown in FIG. 1.

Lens 310 is made of substantially the same material as the corneal onlay 110. The lens 310 is coaxial with the optical axis of the eye and is placed and secured in the stroma 313 using conventional surgical procedures. Lens 310 is structured to correct one or more vision problems caused by defects in cornea 314 or in one or more other components of the eye.

After lens 310 is surgically implanted to stroma 313 as shown in FIG. 3, the lens 310 becomes adhered to the tissue of the stroma. Ultimately, the stroma 313 is securely attached to lens 310.

The following non-limiting examples illustrate certain features of the present invention.

EXAMPLE 1

Lyophilized collagen (1.0 g) was hydrated for 18 hours with sterile water (17.0 g). A small amount of glacial acetic acid (100 uL) added to the collagen gel renders the gel optically clear. Methyl methacrylate (2.0 g) and ethylene glycol dimethacrylate (0.06 g) were thoroughly mixed into the clear collagen gel. This mixture then degassed under vacuum (2–3 mins.) and centrifuged to provide a slightly opaque homogeneous gel. This mixture has a composition (in weight percent) of 85% water, 10% methyl methacrylate, 5% collagen, and 0.3% ethylene glycol dimethacrylate. The monomer/collagen gel mixture was transferred to polypropylene molds and cured using 1 MRad of gamma radiation. The molds were opened and the cured collagen composite was neutralized in an aqueous 2% sodium bicarbonate solution for 4 hours. The neutralized composite was then washed with water 3 times over 3 days.

The resulting composite formed a hydrogel which had an equilibrium water content of 92% with an effective glucose diffusivity of $2.9 \times 10^{-6}$ cm$^2$/sec and a tensile strength of 118 g/mm$^2$. This material had a cell migration index of 1.6 (rabbit epithelial cells migrated (in vitro) 1.6 times faster on this composite than on tissue culture polystyrene).

EXAMPLES 2 TO 8

Example 1 was repeated seven (7) times except that the components in the mixture were varied. The components included in each of these mixtures, together with results obtained from the hydrogel formed from each composite are shown in Table 1 (the results from Example 1 are also shown in Table 1).

TABLE 1

| Example | Collagen wt % | Monomer wt % | Cross-Linker | EWC[1] | GD[2] | CM[3] |
|---|---|---|---|---|---|---|
| 1 | 5 | MMA[4], 10 | EGD[6], 0.3 | 92.0 | 2.9 | 1.60 |
| 2 | 5 | MMA, 2.5 | EGD, 0.3 | 94.2 | 7.5 | 1.21 |
| 3 | 5 | MMA, 5.0 | EGD, 0.3 | 93.4 | 7.6 | 1.44 |
| 4 | 5 | MMA, 10 | EGD, 0.3 | 92.9 | 13.0 | — |
| 5 | 5 | MMA, 2.5 | BIS[7], 0.3 | 94.3 | 8.2 | 1.21 |
| 6 | 5 | MMA, 5.0 | BIS, 0.3 | 94.1 | 14.0 | 1.50 |
| 7 | 5 | — | — | 94.1 | 5.5 | 1.78 |
| 8 | 5 | DMA[5], 5.0 | BIS, 0.3 | 95.7 | 11.0 | 0.83 |
| 9 | 5 | — | — | 94.1 | 9.2 | 1.39 |

[1]The equilibrium water content of the hydrogel composition, in weight percent
[2]Glucose diffusivity in 10$^{-6}$ cm$^2$/sec.
[3]Cell Migration Index
[4]Methyl methacrylate
[5]Dimethyl methacrylate
[6]Ethylene glycol dimethacrylate
[7]N,N'-methylenebisacrylamide The results indicate that formulating hydrophobic polymeric materials into a collagen composite (Example 1 to 6 and 8) provides generally as good or better glucose diffusivity and/or cell migration (cytophilicity) as a collagen composite without such hydrophobic polymeric material (Examples 7 and 9). In addition, the optical clarity and good mechanical strength of the collagen composite is maintained after hydrophobic polymeric material incorporation. One important advantage of incorporating a hydrophobic polymeric material into a collagen composite is that such "mixed" composite has enhanced or improved biostability (resistance to digestion by enzymes) relative to the collagen composite without the hydrophobic polymeric material.

EXAMPLES 9 TO 18

Using the procedure described in Example 1, a series of ten (10) composite disks were prepared. Each of the mixture included 5 wt % collagen, 10 wt % methyl methacrylate and 0.3 wt % ethylene glycol dimethacrylate. In addition, the following components were included in the various individual mixtures.

| Example[1] | |
|---|---|
| 9 | — |
| 10 | Glycidyl methacrylate, 1 wt % |
| 11 | Glycidyl methacrylate, 0.1 wt % |
| 12 | Acrolein, 0.5 wt % |
| 13 | Acrolein, 0.5 wt %; Glycidyl methacrylate, 0.2 wt % |
| 14 | Acrolein, 1 wt % |
| 15 | Acrolein, 1 wt %; polyamine, 0.5 wt % |
| 16 | Glycidyl methacrylate, 0.1 wt %; polyamine, 0.5 wt % |
| 17 | Glycidyl methacrylate, 0.1 wt %; acrolein, 0.1 wt % |
| 18[2] | Cinnamaldehyde, 2 wt % |

[1]The balance of each mixture was water.
[2]This mixture included only 8 wt % of methyl methacrylate.

Each of these disks was tested for enzyme resistance by immersing the disk in a buffered aqueous medium containing the enzyme elastase. The amount of disk degradation was determined by measuring the area of the disk after 48 hours exposure to the medium relative to the original disk area. The elastase concentration was set so that a disk of pure collagen was completely degraded in 24 hours.

Results of those biostability tests are shown in Table 2.

TABLE 2

| Example | % Degradation |
|---|---|
| 9 | 66 |
| 10 | 20 |
| 11 | 49 |
| 12 | 26 |
| 13 | 15 |
| 14 | 8,0 |
| 15 | 3 |
| 16 | 26 |
| 17 | 39 |
| 18 | 26 |

These results indicate that the use of a polymeric material, such as PMMA, provides enhanced biostability or enzyme resistance relative to a disk, for example, a collagen disk, without the polymeric material. In addition, the inclusion of one or more bifunctional monomers in the reaction mixture results in further increases in the biostability of the composite disks. The equilibrium water content, glucose diffusivity and cell migration index of each of these composites is acceptable for corneal implant materials of construction.

EXAMPLES 19 TO 21

Example 1 was repeated an additional three (3) times except that an additional material was added to increase the solubility of the methyl methacrylate in the mixture. In Example 21, 12% by weight (instead of 10% by weight) of methyl methacrylate was employed.

Each of the resulting hydrogels was tested for enzyme degradation (as described in Example 9 to 18). Results of these tests are as shown in Table 3.

TABLE 3

| Example | Formulation | % Degradation |
|---|---|---|
| 19 | 0.5% (wt) acrolein; 5% (wt) sucrose | 38 |
| 20 | 0.5% (wt) acrolein; 5% (wt) dextran[1] | 29 |
| 21 | 3% (wt) methyl vinyl ketone | 39 |

[1]Molecular weight is 9000 daltons.

These formulations, that is the formulations of Examples 19, 20 and 21, have enhanced biostability relative to a hydrogel composition produced in accordance with Example 9. Although these formulations are not as biostable as the formulation of Example 12 (which is derived from a mixture containing 0.5 wt % of acrolein), the use of such additional components, that is sucrose, dextran and methyl vinyl ketone, allows a further degree of flexibility in tailoring or customizing the properties of the present compositions to meet the requirements of a specific application. In short, the present compositions can be formed in a controlled and flexible manner so that the properties of the compositions can be predictably altered to suit the particular application involved.

Thus, the present "mixed" composites provide optically clear hydrogels having high water contents and sufficient mechanical strength, glucose diffusivity, cytophilicity and biostability to be useful as synthetic epikeratophakia lenses. Further, the properties, such as the optical properties, water content, glucose diffusivity, cytophilicity and biostability, of the hydrogel compositions of the present invention can be adjusted by using different amounts and types of collagen, monomers, bifunctional monomers and cross-linkers, as well as by using different polymerization and initiation methods.

While this invention has been described with respect to various specific examples and embodiments, it is to be understood that the invention is not limited thereto and that it can be variously practiced within the scope of the following claims.

What is claimed is:

1. A corneal implant comprising a lens body which is optically clear and is structured to be surgically attached in or on the cornea of a mammalian eye, said lens body including a hydrogel composition comprising water, a collagen component and a polymeric material covalently bonded to said collagen component, said polymeric material being present in an amount at least equal to the amount, by weight, of said collagen component, having increased hydrophobicity relative to said collagen component, and being derived from the polymerization of a monomeric component having a fractional polarity equal to or less than the fractional polarity of methyl methacrylate, and said hydrogel composition having enhanced biostability relative to an identical hydrogel composition without said polymeric material.

2. The corneal implant of claim 1 wherein said polymeric material is cross-linked and is grafted onto said collagen component, and said hydrogel composition includes at least about 60% by weight of water.

3. The corneal implant of claim 1 wherein said polymeric material is distributed throughout said collagen component.

4. The corneal implant of claim 1 wherein said hydrogel composition further comprises a linked component covalently bonded to said collagen component and said polymeric material and being effective to further enhance the biostability of said hydrogel composition relative to an identical hydrogel composition without said linked component.

5. The corneal implant of claim 1 wherein said lens body is structured to be surgically attached on the cornea of a mammalian eye.

6. The corneal implant of claim 1 wherein said polymeric material is derived from the polymerization of a monomeric component including one or more compounds having functional carbon-carbon unsaturation.

7. The corneal implant of claim 1 wherein said polymeric material is derived from the polymerization of a monomeric component selected from the group consisting of olefins, acrylates, methacrylates, substituted counterparts thereof and mixtures thereof.

8. A corneal implant comprising a lens body which is optically clear and is structured to be surgically attached in or on the cornea of a mammalian eye, said lens body including a hydrogel composition comprising water, a collagen component and a polymeric material covalently bonded to said collagen component, said polymeric material having increased hydrophobicity relative to said collagen component and being derived from a monomeric component having a fractional polarity equal to or less than the fractional polarity of methyl methacrylate, said hydrogel composition having enhanced biostability relative to an identical hydrogel composition without said polymeric material.

9. The corneal implant of claim 8 wherein said polymeric material is cross-linked and is grafted onto said collagen component, and said hydrogel composition includes at least about 60% by weight of water.

10. The corneal implant of claim 8 wherein said hydrogel composition further comprises a linked component covalently bonded to said collagen component and said polymeric material and being effective to further enhance the biostability of said hydrogel composition relative to an identical hydrogel composition without said linked component, said linked component being derived from a bifunctional monomeric component.

11. The corneal implant of claim 8 wherein said polymeric material is derived from the polymerization of a monomeric component selected from the group consisting of olefins, acrylates, methacrylates, substituted counterparts thereof and mixtures thereof.

12. The corneal implant of claim 8 wherein said polymeric material is distributed throughout said collagen component and is present in an amount at least equal to the amount, by weight, of said collagen component.

13. The corneal implant of claim 8 wherein said hydrogel composition further comprises a linked component covalently bonded to said collagen component and said polymeric material and being effective to further enhance the biostability of said hydrogel composition relative to an identical hydrogel composition without said linked component, said linked component being derived from a bifunctional monomeric component.

* * * * *